United States Patent [19]

Yoshioka et al.

[11] Patent Number: 5,409,583
[45] Date of Patent: Apr. 25, 1995

[54] METHOD FOR MEASURING CONCENTRATIONS OF SUBSTRATES IN A SAMPLE LIQUID BY USING A BIOSENSOR

[75] Inventors: Toshihiko Yoshioka, Osaka; Satoko Fujisawa; Mariko Miyahara, both of Moriguchi; Shiro Nankai, Hirakata, all of Japan

[73] Assignee: Matsushita Electric Industrial Co., Ltd., Kadoma, Japan

[21] Appl. No.: 128,852

[22] Filed: Sep. 28, 1993

[30] Foreign Application Priority Data

Sep. 30, 1992 [JP] Japan .................................. 4-261183

[51] Int. Cl.$^6$ ............................................. G01N 27/26
[52] U.S. Cl. ................................ 204/153.12; 204/153.1
[58] Field of Search ................ 204/153.12, 153.1, 403, 204/418; 435/817, 288, 291

[56] References Cited

U.S. PATENT DOCUMENTS

| 5,135,876 | 8/1992 | Andrade | 436/518 |
| 5,192,415 | 3/1993 | Yoshioka et al. | 204/403 |
| 5,264,103 | 11/1993 | Yoshioka et al. | 204/403 |
| 5,264,103 | 11/1993 | Yoshioka et al. | 204/403 |

FOREIGN PATENT DOCUMENTS 0125136  11/1984  European Pat. Off. .
3202764  9/1991  Japan .

OTHER PUBLICATIONS

Search Report for European Appln. 931/5800.0, Mailed Jan. 12, 1994.

Primary Examiner—John Niebling
Assistant Examiner—Bruce F. Bell
Attorney, Agent, or Firm—Renner, Otto, Boisselle & Sklar

[57] ABSTRACT

The present invention provides a method for measuring concentrations of the first and second substrates in a sample liquid by using a biosensor. The biosensor has an electrically insulating substrate, an electrode system, and a reaction layer including a first enzyme, a second enzyme and an electron acceptor. The method includes the steps of measuring a response current value $I_1$ of a predetermined period of time $T_1$ after supplying the sample liquid including the first and second substrates to the biosensor; measuring a response current value $I_2$ of a predetermined period of time $T_2$ after the supply of the sample liquid; obtaining the concentration $C_1$ of the first substrate corresponding to the current value $I_1$ based on the previously determined relationship between the concentration of the first substrate and the response current value of the predetermined period of time $T_1$ after the supply; obtaining a response current value $I_1'$ corresponding to the concentration $C_1$ of the first substrate in the sample liquid based on the previously determined relationship between the concentration of the first substrate and the response current value of the predetermined period of time $T_2$ after the supply; and obtaining the concentration $C_2$ of the second substrate in the sample liquid corresponding to the current value calculated by subtracting the current value $I_1'$ from the current value $I_2$ based on the previously determined relationship between the concentration of the second substrate and the response current value of the predetermined period of time $T_2$ after the supply.

20 Claims, 4 Drawing Sheets

METHOD FOR MEASURING CONCENTRATIONS OF SUBSTRATES IN A SAMPLE LIQUID BY USING A BIOSENSOR

BACKGROUND OF THE INVENTION

1. Field of the Invention

The present invention relates to a method for measuring a concentration, of a substrate in a sample liquid by allowing the substrate to react with an enzyme that can specifically react with the substrate and then quantifying, after a predetermined period of time, the change in the concentration of a material that has been changed through the reaction. More particularly, the present invention relates to an accurate, rapid and easy method for measuring concentrations of a plurality of substrates, such as sucrose and glucose, contained in a sample liquid, such as fruit juice, blood, lymph and urine, by utilizing specific catalyses of enzymes in one biosensor.

2. Description of the Related Art

Various types of biosensors utilizing specific catalyses of enzymes have been recently developed. Such biosensors are advantageous in measuring a concentration of a substrate in various sample liquids, such as fruit juice, blood., lymph and urine, because they have sufficient specificity to each substrate in order to attain an accurate measurement and because they can achieve relatively easy and rapid quantification of the substrate.

Japanese Laid-Open Patent Publication No. 3-202764 and U.S. Pat. No. 5,192,415 disclose the following method for measuring a concentration of a substrate in a sample liquid by using a biosensor:

The biosensor has an insulating substrate, an electrode system including a working electrode and a counter electrode formed on the substrate, and a reaction layer including a hydrophilic polymer, an enzyme and an electron acceptor formed on the electrode system. When a sample liquid containing a substrate to be quantified is supplied to the biosensor, the enzyme and the electron acceptor in the reaction layer react with the sample liquid. The change in the concentration of a material through this reaction is electrochemically detected by the electrode system. Thus, the concentration of the substrate in the sample liquid is measured.

A glucose sensor will now be described as an example of this type of biosensor.

In the glucose sensor, glucose oxidase is used as an enzyme in the reaction layer. When a sample liquid containing glucose is supplied to the glucose sensor, the reaction layer is dissolved in the sample liquid. The glucose in the sample liquid is oxidized by glucose oxidase in the reaction layer. At the same time, the electron acceptor in the reaction layer is reduced. After the oxidation reaction of glucose in the sample liquid is completed, a fixed voltage is applied between the working electrode and the counter electrode in the electrode system, thereby oxidizing the reduced electron acceptor. By measuring an oxidation current caused by the application of the voltage is measured to quantify the concentration of the glucose in the sample liquid.

However, this conventional quantification method can be applied only when one kind of substrate in a sample liquid is desired to be quantified. It is impossible to measure concentrations of a plurality of substrates in a sample liquid at one time.

When a plurality of substrates in a sample liquid are to be quantified, it is necessary to use a plurality of biosensors respectively using different enzymes that can specifically react with the respective substrates. Alternatively, it is necessary to use a biosensor having a plurality of electrode systems and reaction layers containing different enzymes that can specifically react with the respective substrates. The present inventors filed U.S. patent application Ser. No. 07/961,528 (filed on Oct. 15, 1992) disclosing the latter type of biosensor. In this manner, usage of a plurality of biosensors or complication of the structure of a biosensor can not be avoided in order to quantify a plurality of substrates in a sample liquid.

SUMMARY OF THE INVENTION

The method for measuring concentrations of a first substrate and a second substrate in a sample liquid by using a biosensor having an electrically insulating substrate, an electrode system including a working electrode and a counter electrode formed on the insulating substrate, and a reaction layer including a first enzyme that can specifically react with the first substrate, a second enzyme that can specifically react with the second substrate and an electron acceptor of the present invention comprises the steps of:

(a) determining a relationship between a concentration of the first substrate and a response current value measured with an auxiliary testing biosensor having the same structure as the biosensor, the response current value being measured after a predetermined period of time $T_1$, $T_1$ beginning upon supplying a solution including the first substrate to the auxiliary testing biosensor;

(b) determining a relationship between the concentration of the first substrate and a response current value measured with the auxiliary testing biosensor after a predetermined period of time $T_2$, $T_2$ beginning upon supplying the solution including the first substrate;

(c) determining a relationship between a concentration of the second substrate and a response current value measured with another auxiliary testing biosensor having the same structure as the biosensor, the response current value being measured after the predetermined period of time $T_2$, $T_2$ beginning upon supplying a solution including the second substrate to the auxiliary testing biosensor;

(d) supplying a sample liquid including the first and second substrates to the biosensor and applying a voltage between the working electrode and the counter electrode in the electrode system after the predetermined period of time $T_1$, $T_1$ beginning upon supplying the sample liquid, for measuring a response current value $I_1$;

(e) applying a voltage between the working electrode and the counter electrode in the electrode system after the predetermined period of time $T_2$, $T_2$ beginning upon supplying the sample liquid, for measuring a response current value $I_2$;

(f) obtaining a concentration $C_1$ of the first substrate in the sample liquid corresponding to the current value $I_1$ based on the relationship between the concentration of the first substrate and the response current value determined in step (a);

(g) obtaining a response current value $I_1'$ corresponding to the concentration $C_1$ of the first substrate in the sample liquid based on the relationship between the concentration of the first substrate and the response current value determined in step (b); and (h) obtaining a concentration $C_2$ of the second substrate in the sample liquid corresponding to a current value calculated by subtracting the current value $I_1'$ from the current value $I_2$ based on the relationship between the concentration of the second substrate and the response current value determined in step (c).

In one embodiment, the predetermined period of time $T_1$ is a time having a sufficient length for at least part of the first substrate to react with the first enzyme and a time for the second substrate not to substantially react with the second enzyme; and the predetermined period of time $T_2$ is a time having a sufficientl length for at least part of the second substrate to react with the second enzyme.

In one embodiment, the first enzyme is glucose oxidase and the second enzyme is hydrolase of sucrose.

In one embodiment, the first enzyme is fructose dehydrogenase and the second enzyme is hydrolase of sucrose.

In one embodiment, the first enzyme is glucose oxidase, and the second enzyme is selected from the group consisting of alkaline phosphatase, maltase, $\beta$-galactosidase and cellulase.

In one embodiment, the steps (a), (b) and (c) of determining the relationships between the concentrations of the first and the second substrates and the response current values further comprises the steps of:

supplying a plurality of solutions including the first or the second substrate respectively at known concentrations to a plurality of the auxiliary testing biosensors;

applying a voltage between the counter electrode and the working electrode of each auxiliary testing biosensor after the predetermined periods of time $T_1$ and $T_2$, $T_1$ and $T_2$ beginning upon supplying each solution to each of the auxiliary testing biosensors; and measuring current values of a predetermined period of time after applying the voltage.

In another aspect of the present invention, the method comprises the steps of:

(a) obtaining a response curve a indicating a relationship between a concentration of the first substrate and a response current value measured with an auxiliary testing biosensor after a predetermined period of time $T_1$, $T_1$ beginning upon supplying a solution including the first substrate to the auxiliary testing biosensor, the predetermined period of time $T_1$ being a time required for at least part of the first substrate to react with the first enzyme;

(b) obtaining a response curve b indicating a relationship between the concentration of the first substrate and a response current value measured with the auxiliary testing biosensor after a predetermined period of time $T_2$, $T_2$ beginning upon supplying the solution including the first substrate to the auxiliary testing biosensor, the predetermined period of time $T_1$ being a time required for at least part of the second substrate to react with the second enzyme;

(c) obtaining a response curve d indicating a relationship between a concentration of the second substrate and a response current value measured with the auxiliary testing biosensor after the predetermined period of time $T_2$, $T_2$ beginning upon supplying the solution including the second enzyme;

(d) applying a voltage between the working electrode and the counter electrode in the electrode system after the predetermined period of time $T_1$, $T_1$ beginning upon supplying the sample liquid including the first substrate and the second substrate to the biosensor, to measure a response current value $I_1$;

(e) applying a voltage between the working electrode and the counter electrode in the electrode system after the predetermined period of time $T_2$, $T_2$ beginning upon supplying the sample liquid including the first substrate and the second substrate to the biosensor, to measure a response current value $I_2$;

(f) obtaining a concentration of the first substrate in the sample liquid corresponding to the current value $I_1$ based on the response curve a obtained in step (a);

(g) obtaining a response current value $I_1'$ corresponding to the concentration $C_1$ of the first substrate in the sample liquid based on the response curve b obtained in step (b); and (h) obtaining a concentration $C_2$ of the second substrate in the sample liquid corresponding to the current value calculated by subtracting the current value $I_1'$ from the current value $I_2$ based on the response curve d obtained in step (c).

In one embodiment, the predetermined period of time $T_1$ is 30 seconds or less and the predetermined period of time $T_2$ is 50 seconds or more.

Thus, the invention described herein makes possible the advantages of (1) providing an accurate, rapid and easy method for measuring concentrations of a plurality of substrates in a sample liquid by using one biosensor; and (2) providing a method for measuring concentrations of a plurality of substrates in a sample liquid with ease by using a biosensor having a comparatively simple structure.

These and other advantages of the present invention will become apparent to those skilled in the art upon reading and understanding the following detailed description with reference to the accompanying figures.

DESCRIPTION OF THE PREFERRED EMBODIMENTS

A biosensor used in the present invention comprises an electrically insulating substrate, an electrode system including a working electrode and a counter electrode formed on the substrate, and a reaction layer provided in contact with or in the vicinity of the electrode system.

The insulating substrate can be formed of a synthetic resin board such as a polyethylene terephthalate board.

The electrode system including the working electrode and the counter electrode can be formed on the substrate by any known method. For example, leads are formed on the substrate, and then the working electrode and the counter electrode are formed so as to connect to each lead and to be insulated from each other. The electrode system can be a two-electrode system or a three-electrode system including an additional reference electrode. Generally in the three-electrode system, more precise values are obtained.

The reaction layer can be provided over or in the vicinity of the, electrode system, and generally covers at least part of the working electrode and the counter electrode.

The reaction layer includes at least a first enzyme, a second enzyme and an electron acceptor. The reaction layer can be formed from one uniform layer, or can be formed from a first layer including a hydrophilic polymer, and a second layer including at least the first enzyme, the second enzyme and the electron acceptor and formed on the first layer.

Examples of the hydrophilic polymer contained in the first layer include carboxymethyl cellulose, hydroxyethyl cellulose, hydroxypropyl cellulose, methyl cellulose, ethyl cellulose, ethyl hydroxyethyl cellulose, carboxymethyl ethyl cellulose, polyvinylpyrrolidone, polyvinyl alcohol, gelatin or its derivatives, acrylic acid or its salts, methacrylic acid or its salts, starch or its derivatives and maleic anhydride or its salts. Among the above, carboxymethyl cellulose, hydroxyethyl cellulose, hydroxypropyl cellulose, methyl cellulose, ethyl cellulose, ethyl hydroxyethyl cellulose, carboxymethyl ethyl cellulose are preferred.

The kinds of the first and second enzymes contained in the reaction layer depend upon the particular substrate to be quantified. Glucose oxidase, fructose dehydrogenase or the like is typically used as the first enzyme. As the second enzyme, hydrolase of sucrose, alkaline phosphatase, maltase, $\beta$-galactosidase, cellulase or the like is used. Specifically, invertase is used as the second enzyme in the quantification of sucrose; alkaline phosphatase is used in the quantification of glucose-6-phosphate; maltase is used in the quantification of maltose; $\beta$-galactosidase is used in the quantification of lactose; and cellulase is used in the quantification of cellulose.

It is preferable to select the first and second enzymes in order to make the oxidizing rate of $\beta$-glucose by the first enzyme significantly different from the hydrolyzing rate of the substrate by the second enzyme. Specifically, in the quantification of sucrose and glucose in a sample liquid, a preferable combination of enzymes is invertase and glucose oxidase; and in the quantification of sucrose and fructose, a preferable combination of enzymes is invertase and fructose dehydrogenase. The reaction layer can further contain mutarotase, for accelerating the isomerization from $\alpha$-glucose to $\beta$-glucose, as an enzyme.

The electron acceptor contained in the reaction layer is reduced by electrons generated in the oxidation reaction caused by the enzyme. Examples of the electron acceptor include potassium ferricyanide, p-benzoquinone, phenazinemethosulfate, methylene blue and ferrocene. The electron acceptor can be one of the examples above, or a combination of two or more of the examples above.

The enzymes and the electron acceptor in the reaction layer can be dissolved in a supplied sample liquid. Alternatively, the enzymes and the electron acceptor can be immobilized on the insulating substrate or the like to be insoluble in the sample liquid.

The reaction layer can further contain a pH buffer. Examples of the pH buffer include potassium dihydrogenphosphate-dipotassium hydrogenphosphate, potassium dihydrogenphosphate-disodium hydrogenphosphate, sodium dihydrogenphosphate-dipotassium hydrogenphosphate, sodium dihydrogenphosphate-disodium hydrogenphosphate, citric acid-disodium hydrogenphosphate, citric acid-dipotassium hydrogenphosphate, citric acid-sodium citrate, citric acid-potassium citrate, potassium dihydrogencitrate-sodium hydroxide, sodium dihydrogencitrate-sodium hydroxide, sodium hydrogenmaleate-sodium hydroxide, potassium hydrogenphthalate-sodium hydroxide, succinic acid-sodium tetraborate, maleic acid-tris(hydroxymethyl)aminomethane, tris(hydroxymethyl)aminomethane-tris(hydroxymethyl)aminomethane hydrochloride, [N-(2-hydroxyethyl)piperazine-N'-2-ethanesulfonic acid]-sodium hydroxide, [N-tris(hydroxymethyl)methyl-2-aminoethanesulfonic acid]-sodium hydroxide, and [piperazine-N,N'-bis(2-ethanesulfonic acid)]-sodium hydroxide.

The reaction layer can be formed by dropping a solution, including at least the enzymes and the electron acceptor, onto the substrate and then drying the dropped solution.

When the reaction layer comprises the first and second layers, the second layer can be formed by dropping a mixed solution, including at least the first and second enzymes and the electron acceptor, onto the first layer, and then drying the mixed solution. When the mixed solution is dropped onto the first layer including, for example, carboxymethyl cellulose, the first layer is once dissolved in and superficially mixed with the mixed solution. However, since the reaction layer including the first and second layers is neither stirred nor uniformly mixed, the surface of the electrode system is allowed to be in contact with the first layer alone. Therefore, the enzymes and the electron acceptor contained in the second layer do not come in contact with the surface of the electrode system. Thus, response degradation and variation due to adsorption of proteins onto the surface of the electrode system and the like can be avoided.

When a saccharide in a sample liquid is quantified by using this type of biosensor, the saccharide is hydrolyzed by the second enzyme to generate $\alpha$-glucose. The isomerization from $\alpha$-glucose to $\beta$-glucose is accelerated by an enzyme such as mutarotase. The thus generated $\beta$-glucose is oxidized by the first enzyme. The electron acceptor is reduced by the electrons transferred through the oxidation reaction caused by the first enzyme. The amount of the reduced electron acceptor is electrically measured.

A solution including a first substrate with a known concentration is supplied to the above-described biosensor. A fixed voltage on the basis of the voltage at the counter electrode is applied to the working electrode after a predetermined period of time $T_1$, which begins upon the supply of the solution, and after a predetermined period of time $T_c$, which begins upon the application of the voltage, a response current value is measured. The current value increases as the concentration of the first substrate in the solution becomes higher. A number of solutions respectively including the first substrate at different known concentrations are quantified to obtain the respective response current values. Thus, the relationship between the concentration of the first substrate in the solution and the current value measured when a voltage is applied after the predetermined period of time $T_1$, which begins upon the supply of the solution (hereinafter referred to as the "current value after the time $T_1$"), is obtained as a response curve a in FIG. 1.

Similarly, a fixed voltage on the basis of the voltage at the counter electrode is applied again to the working electrode after a predetermined period of time $T_2$, which begins upon the supply of the solution. Then, a current value after the predetermined period of time $T_c$, which begins upon the application of the voltage, is measured to obtain the relationship between the concentration of the first substrate and the response current value measured when a voltage is applied after the predetermined period of time $T_2$, which begins upon the supply of the solution (hereinafter referred to as the "current value after the time $T_2$"), is obtained as a response curve b in FIG. 1.

Next, another biosensor with the same structure is supplied with a solution including a second substrate at a known concentration in the same manner as above. A fixed voltage on the basis of the voltage at the counter electrode is applied to the working electrode after the predetermined period of time $T_1$, and a current value after the predetermined period of time $T_c$, which begins upon the application of the voltage, is measured. A number of solutions respectively including the second substrate at different known concentrations are quantified to obtain the respective response current values. The results are shown as a response curve c in FIG. 1. These current values do not depend upon the concentration of the second substrate and are approximately constant.

Figure 1:
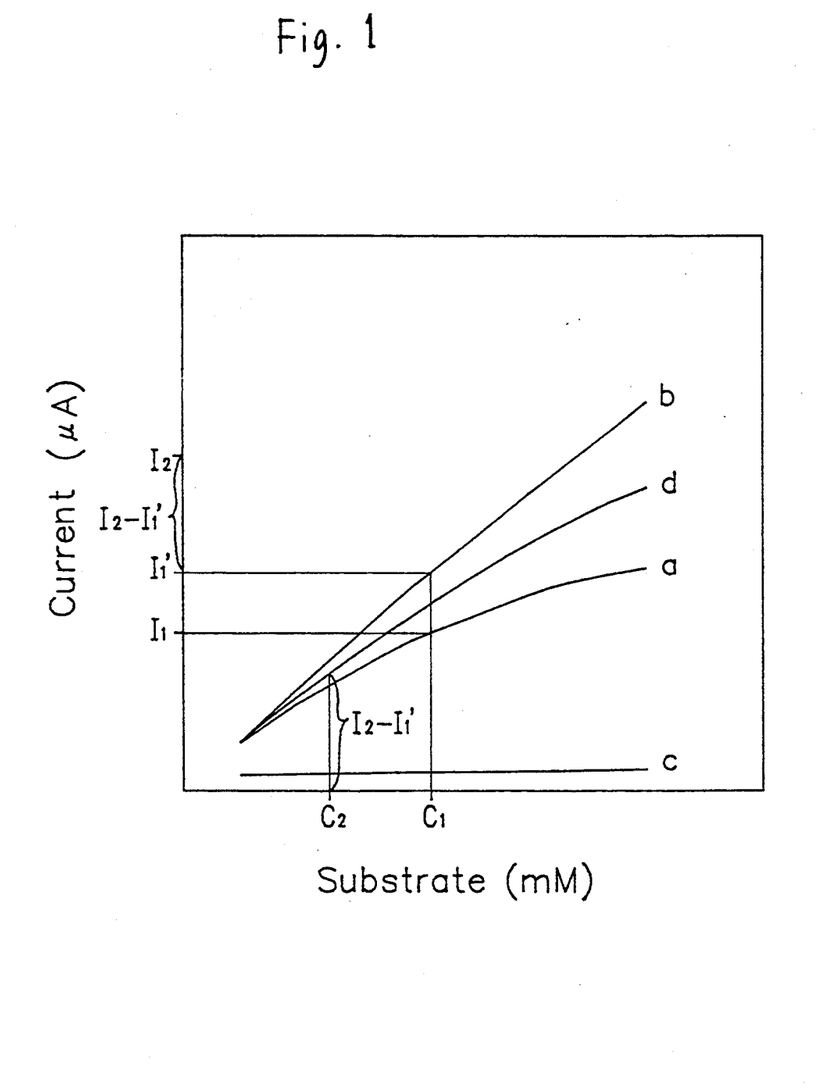
FIG. 1 is a graph showing the relationship between a concentration of a substrate in a sample liquid and a response current value obtained by a biosensor of the present invention.

Similarly, the current values after the time $T_2$ are measured to obtain the results shown as a response curve d in FIG. 1. The current values increase as the concentration of the second substrate in the solution becomes higher.

The time $T_1$ is generally a time sufficiently long for the second substrate not to substantially react with the second enzyme and for at least part of the first substrate to react with the first enzyme. The time $T_2$ is a time sufficiently long for at least part of the second substrate to react with the second enzyme.

In this manner, the relationships between the concentrations of the first and second substrates and the current values after the times $T_1$ and $T_2$ can be obtained as the response curves a through d in FIG. 1.

Next, a method for measuring unknown concentrations of the first and second substrates contained in the sample liquid will be described.

After supplying the sample liquid to the biosensor, current values after the time $T_1$ and the time $T_2$ are measured in the same manner as described above to obtain the current values $I_1$ and $I_2$.

When the obtained current value $I_1$ is applied to the response curve a in FIG. 1, the concentration $C_1$ of the first substrate in the sample liquid can be determined. The concentration $C_1$ is then applied to the response curve c to obtain a current value $I_1'$ after the time $T_2$ of the second substrate. The value calculated by subtracting the obtained current value $I_1'$ from the current value $I_2$ is the current value based on the second substrate alone. Therefore, when the value $I_2 - I_1'$ is applied to the response curve d, the concentration $C_2$ of the second substrate can be determined.

The times $T_1$ and $T_2$ optionally vary depending upon the identity and the concentrations of the first and second substrates and the identity of the first and second enzymes. For example, when the first and second substrates are glucose and sucrose, respectively, the times $T_1$ and $T_2$ are preferably 30 seconds or less and 50 seconds or more, respectively. Further, the time period $T_c$ is, for example, 1 to 10 seconds.

By appropriately selecting the first and second enzymes, the biosensor of this invention can be used for quantifying various substrates. For example, the biosensor can be used for quantifying a combination of glucose-6-phosphate and glucose by using alkaline phosphate and glucose oxidase as the enzymes, a combination of maltose and glucose by using maltase and glucose oxidase as the enzymes, a combination of lactose and glucose by using β-galactosidase and glucose oxidase as the enzymes, and a combination of cellulose and glucose by using cellulase and glucose oxidase as the enzymes.

In this manner, according to this invention, a plurality of substrates in a sample liquid can be quantified accurately, rapidly and easily in one biosensor by previously determining the relationships between the concentrations of the substrates to be quantified and the response current values of the biosensor. Thus, it is possible to quantify various saccharides in food, such as fruit, blood, lymph, urine and the like by using one biosensor.

EXAMPLES

Throughout the drawings mentioned in the following description of the examples, the same element has a common reference numeral. Part of the description is omitted as occasion demands.

Example 1

A method for measuring concentrations of sucrose and glucose in a sample liquid by a saccharide sensor will now be described.

A. Production of a Saccharide Sensor

Figure 2:
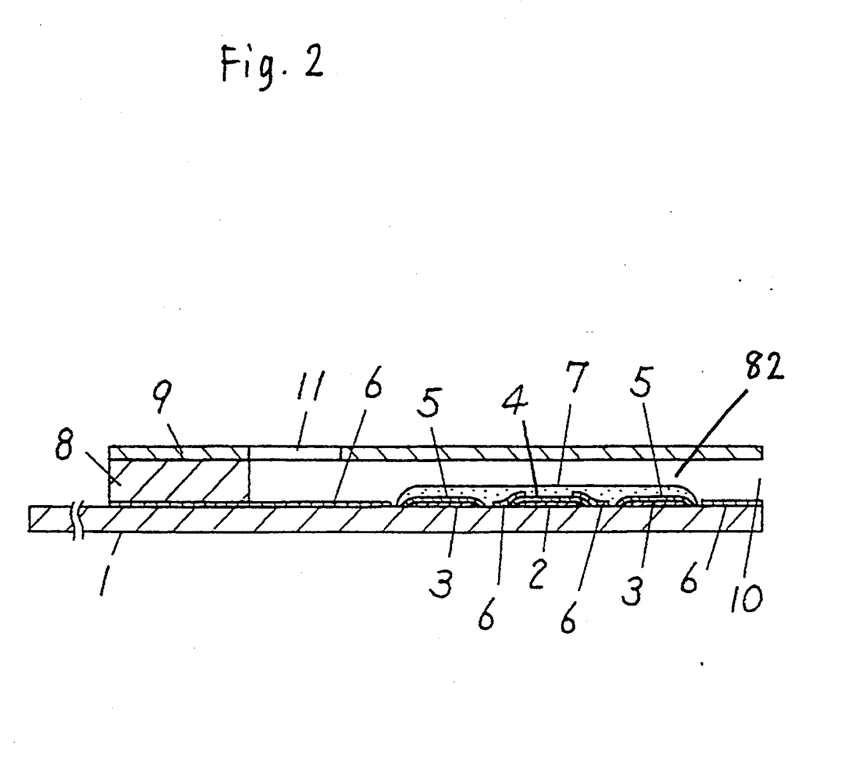
FIG. 2 is a sectional view of a saccharide sensor according to an example of the present invention.
Figure 3:
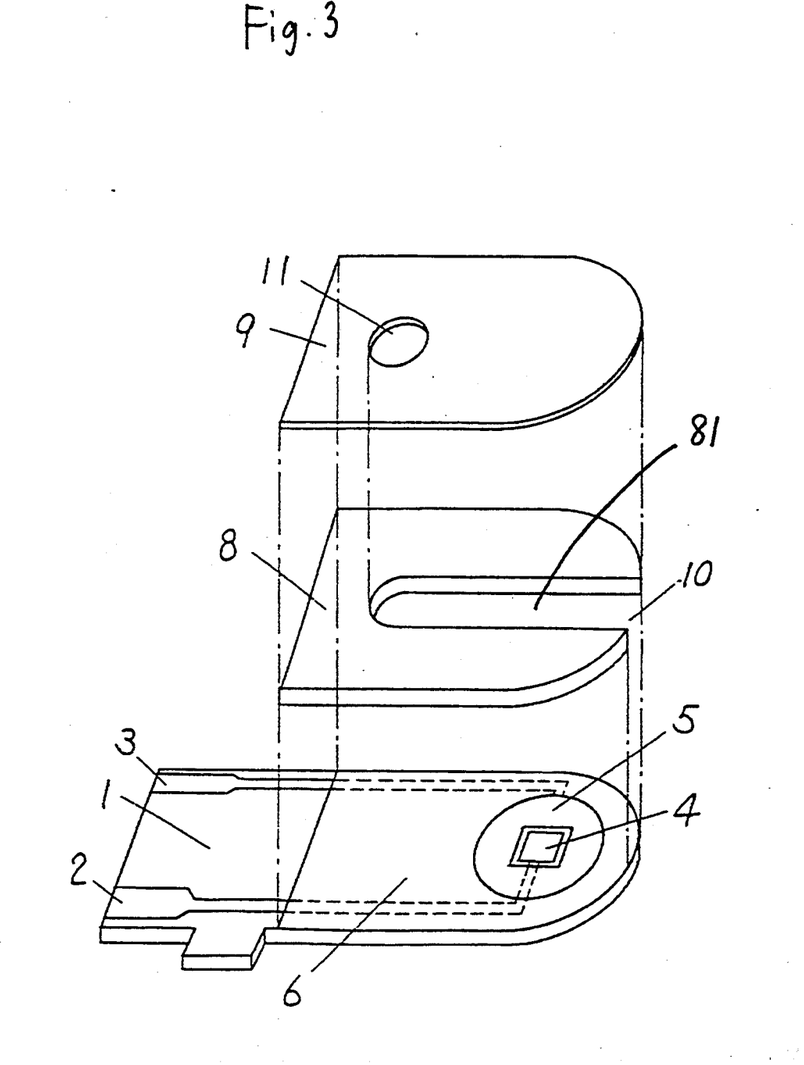
FIG. 3 is an exploded perspective view of the saccharide sensor of FIG. 2 from which a reaction layer is removed.

Silver paste was printed by screen printing on an insulating substrate 1 made from polyethylene terephthalate to form leads 2 and 3 as shown in FIGS. 2 and 3. Conductive carbon paste including a resin binder was printed on the substrate 1 to form a working electrode 4 so as to come in contact with the lead 2. Insulating paste was printed on the substrate 1 to form an insulating layer 6. The insulating layer 6 covered the peripheral portion of the working electrode 4 so as to expose the predetermined area of the working electrode 4. The insulating layer 6 further covered parts of the leads 2 and 3. Next, conductive carbon paste including a resin binder was printed on the insulating layer 6 so as to come in contact with the lead 3, thereby forming a counter electrode 5. Thus, an electrode system including the working electrode 4 and the counter electrode 5 was formed.

Next, a 0.5 wt % aqueous solution of carboxymethyl cellulose sodium salt (hereinafter referred to as "CMC") as a hydrophilic polymer was dropped on the electrode system including the working electrode 4 and the counter electrode 5, and dried to form a CMC layer. A mixed solution, in which invertase (EC3.2.1.26), mutarotase (EC5.1.3.3), and glucose oxidase (EC1.1.3.4; hereinafter referred to as GOD) as enzymes, and potassium ferricyanide as an electron acceptor were dispersed in a phosphate buffer solution (a mixture of 0.2M of $KH_2PO_4$ and 0.2M of $Na_2HPO_4$; pH=7.4), was dropped on the CMC layer, and dried to form a reaction layer 7.

After forming the reaction layer 7 as described above, a cover 9 and a spacer 8 were adhered to the substrate 1 as shown with dashed lines in FIG. 3. Thus, the saccharide sensor was produced. The spacer 8 had a U-shaped groove 81. Therefore, when the cover 9 and the spacer 8 were adhered to the substrate 1, a passage 82 was formed by the groove 81. One end of the passage 82 at the tip of the saccharide sensor served as a sample supply port 10. The other end of the passage 82 was open on the cover 9 and the opening served as an air port 11.

The reaction layer 7 can be provided on the cover 9 or the spacer 8 so as to face the passage 82. Since the sample liquid supplied to the saccharide sensor through the sample supply port 10 fills the passage 82, the reaction layer 7 at such a position can be dissolved in the sample liquid.

B. Drawing a Graph of Response Curves

Figure 4:
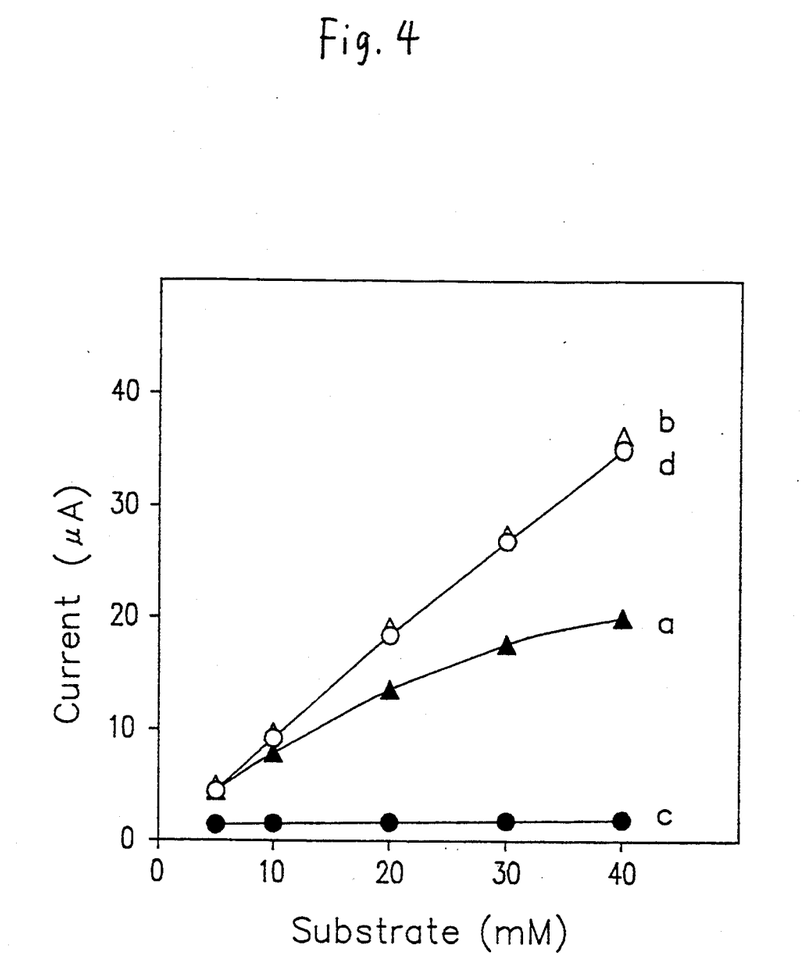
FIG. 4 is a graph showing the relationship between a concentration of a substrate in a sample liquid and a response current value obtained by the saccharide sensor of FIG. 2.

The saccharide sensor produced as above was supplied with 3 μl of an aqueous glucose solution with a known concentration through the sample supply port 10. The glucose solution rapidly reached the air port 11 and the reaction layer 7 on the electrode system was dissolved in the glucose solution. Ten seconds after the supply of the glucose solution, a voltage of +0.5 V on the basis of the voltage at the counter electrode 5 was applied to the working electrode 4, and a current value was measured 5 seconds after application. This procedure was repeated with a plurality of aqueous glucose solutions respectively having different known concentrations to obtain a response curve a as shown in FIG. 4. As illustrated by the response curve a, the current value increases as the glucose concentration becomes higher.

The saccharide sensor of this example has the following response to glucose: When the reaction layer 7 is dissolved in a glucose solution, glucose in the solution is oxidized by GOD in the reaction layer 7. At the same time, potassium ferricyanide is reduced to generate potassium ferrocyanide. By the application of a voltage to the working electrode 4, potassium ferrocyanide is oxidized. The oxidation current caused at this point corresponds to the glucose concentration in the solution.

As a result of the above, it is considered that, in quantifying glucose, the reaction between GOD and glucose proceeds to some extent 10 seconds after the supply of the glucose solution.

Subsequently, 3 minutes after the supply of the glucose solution, a voltage of +0.5 V on the basis of the voltage at the counter electrode 5 was applied again to the working electrode 4, and a response current value was measured 5 seconds after the application. This procedure was also repeated with a plurality of aqueous glucose solutions respectively having different known concentrations to obtain a response curve b as shown in FIG. 4. As illustrated by the response curve b, the current value increases as the glucose concentration becomes higher.

Next, another saccharide sensor having the same structure was supplied through the sample supply port 10 with 3 μl of an aqueous sucrose solution having a known concentration.

Ten seconds after the supply of the sucrose solution, a voltage of +0.5 V on the basis of the voltage at the counter electrode 5 was applied to the working electrode 4, and a current value was measured 5 seconds after the application. This procedure was repeated with a plurality of aqueous sucrose solutions respectively having different known concentrations to obtain a response curve c as shown in FIG. 4. As is apparent from FIG. 4, these current values do not depend upon the sucrose concentration and are constant.

Then, 3 minutes after the supply of the sucrose solution, a voltage of +0.5 V on the basis of the voltage at the counter electrode 5 was applied to the working electrode 4, and a current value was measured 5 seconds after the application. This procedure was repeated with a plurality of aqueous sucrose solutions respectively having different sucrose concentrations to obtain a response curve d as shown in FIG. 4. As illustrated by the response curve d, the current value increases as the sucrose concentration becomes higher.

The saccharide sensor of this example has the following response to sucrose: When the reaction layer 7 is dissolved in the sucrose solution, sucrose in the solution is hydrolyzed by invertase to generate fructose and α-glucose. The α-glucose is isomerized into β-glucose by the catalyses of mutarotase and the β-glucose is oxidized by GOD. At the same time, potassium ferricyanide is reduced to potassium ferrocyanide. The potassium ferrocyanide is oxidized by the application of a voltage of +0.5 V. The oxidation current at this point corresponds to the sucrose concentration. These reactions proceed sufficiently 3 minutes after the supply of the sucrose solution. Accordingly, as illustrated by the response curve d, the current value increases as the sucrose concentration becomes higher.

The enzyme reaction by invertase or mutarotase does not sufficiently proceed 10 seconds after the supply of the sucrose solution, and little β-glucose is generated by this time. Therefore, the current value obtained when a voltage is applied 10 seconds after the supply does not vary depending upon the sucrose concentration as shown with the response curve c in FIG. 4.

C. Measurement of Concentrations of Glucose and Sucrose in a Sample Liquid

To another saccharide sensor having the same structure, 3 μl of a mixed solution of glucose and sucrose respectively having unknown concentrations was supplied through the sample supply port 10.

Ten seconds after the supply of the sample liquid, a voltage of +0.5 V on the basis of the voltage at the counter electrode 5 was applied to the working electrode 4, and a current value was measured 5 seconds after the application. As a result, a current value $I_1$ corresponding only to the glucose concentration was obtained. Then, 3 minutes after the supply of the sample liquid, a voltage of +0.5 V on the basis of the voltage at the counter electrode 5 was applied again to the working electrode 4, and a current value was measured 5 seconds after the application. As a result, a current value $I_2$ corresponding to a sum of the concentrations of glucose and sucrose was obtained.

By using these two current values $I_1$ and $I_2$, respective concentrations of glucose and sucrose in the sample liquid are determined as follows:

When the current value $I_1$ is applied to the response curve a in FIG. 4, the glucose concentration $C_{glu}$ in the sample liquid can be obtained. The current value $I_1'$, which corresponds to the glucose concentration $C_{glu}$ obtained in the case where the voltage was applied 3 minutes after the supply of the sample liquid, can be obtained from the response curve b in FIG. 4. The difference between the current values $I_1'$ and $I_2$, i.e., the value $I_2-I_1'$, is an oxidation current value of glucose generated by hydrolysis of sucrose. Therefore, the sucrose concentration $C_{suc}$ can be obtained by applying the value $I_2-I_1'$ to the response curve d in FIG. 4.

In this manner, the glucose concentration $C_{glu}$ and the sucrose concentration $C_{suc}$ can be accurately obtained from the two current values $I_1$ and $I_2$ by using one saccharide sensor.

Example 2

A method for measuring the concentrations of sucrose and fructose in a sample liquid by using one saccharide sensor will now be described.

In the same manner as in Example 1, the leads 2 and 3, the electrode system including the working electrode 4 and the counter electrode 5, and the insulating layer 6 were formed on the insulating substrate 1 made from polyethylene terephthalate.

Next, a 0.5 wt % aqueous solution including hydroxyethyl cellulose (hereinafter referred to as "HEC") as the hydrophilic polymer was dropped on the electrode system, and dried to form an HEC layer. A mixed solution, in which invertase, fructose dehydrogenase (EC1.1.99.11) and potassium ferricyanide were dispersed in a McIlvaine buffer (a mixture of 0.1M of citric acid and 0.2M of $Na_2HPO_4$; pH=5.5), was dropped on the electrode system, and dried to form the reaction layer 7. Then, the cover 9 and the spacer 8 were adhered to the substrate 1 in the same manner as in Example 1. Thus, a saccharide sensor was produced.

To the saccharide sensor produced as above, 3 μl of a mixed aqueous solution of sucrose and fructose was supplied through the sample supply port 10 as the sample liquid. Ten seconds after the supply of the sample liquid, a voltage of +0.5 V on the basis of the voltage at the counter electrode 5 was applied to the working electrode 4, and a current value was measured 5 seconds after the application, thereby obtaining the response current value corresponding only to the fructose concentration in the sample liquid.

Three minutes after the supply of the sample liquid, a voltage of +0.5 V on the basis of the voltage at the counter electrode 5 was applied again to the working electrode 4, and a current value was measured 5 seconds after the application, thereby obtaining the response current value corresponding to the sum of the concentrations of fructose and sucrose in the sample liquid. As a result, the respective concentrations of fructose and sucrose can be accurately determined as in Example 1 by applying the current values to a graph showing the relationship between the response current values and the concentrations, which has been previously drawn.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for measuring concentrations of a first substrate and a second substrate in a sample liquid by using a biosensor having an electrically insulating substrate, an electrode system including a working electrode and a counter electrode formed on the insulating substrate, and a reaction layer including a first enzyme that can specifically react with the first substrate, a second enzyme that can specifically react with the second substrate and an electron acceptor;

the method comprising the steps of:

(a) determining a relationship between a concentration of the first substrate and a response current value measured with an auxiliary testing biosensor having the same structure as the biosensor, the response current value being measured for a known plurality of solutions having different known concentrations of the first substrate after set period of time $T_1$, $T_1$ beginning upon supplying a solution including the first substrate to the auxiliary testing biosensor;

(b) determining a relationship between the concentration of the first substrate and a response current value measured with the auxiliary testing biosensor after a set period of time $T_2$, $T_2$ beginning upon supplying the solution including the first substrate;

(c) determining a relationship between a concentration of the second substrate and a response current value measured with another auxiliary testing biosensor having the same structure as the biosensor, the response current value being measured for a plurality of solutions having different known concentrations of the second substrate after the set period of time $T_2$, $T_2$ beginning upon supplying a solution including the second substrate to the auxiliary testing biosensor;

(d) supplying a sample liquid including the first and second substrates to the biosensor and applying a voltage between the working electrode and the counter electrode in the electrode system after the set period of time $T_1$, $T_1$ beginning upon supplying the sample liquid, for measuring a response current value $I_1$;

(e) applying a voltage between the working electrode and the counter electrode in the electrode system after the set period of time $T_2$, $T_2$ beginning upon supplying the sample liquid, for measuring a response current value $I_2$;

(f) obtaining a concentration $C_1$ of the first substrate in the sample liquid corresponding to the current value $I_1$ based on the relationship between the concentration of the first substrate and the response current value determined in step (a);

(g) obtaining a response current value $I_1'$ corresponding to the concentration $C_1$ of the first substrate in the sample liquid based on the relationship between the concentration of the first substrate and the response current value determined in step (b); and (h) obtaining a concentration $C_2$ of the second substrate in the sample liquid corresponding to a current value calculated by subtracting the current value $I_1'$ from the current value $I_2$ based on the relationship between the concentration of the second substrate and the response current value determined in step (c).

2. A method according to claim 1, wherein the set period of time $T_1$ is a time for at least part of the first substrate to react with the first enzyme and a time for the second substrate not to substantially react with the second enzyme; and the set period of time $T_2$ is a time for at least part of the second substrate to react with the second enzyme.

3. A method according to claim 2, wherein the set period of time $T_1$ is 30 seconds or less and the set period of time $T_2$ is 50 seconds or more.

4. A method according to claim 1, wherein the first enzyme is glucose oxidase and the second enzyme is hydrolase of sucrose.

5. A method according to claim 1, wherein the first enzyme is fructose dehydrogenase and the second enzyme is hydrolase of sucrose.

6. A method according to claim 1, wherein the first enzyme is glucose oxidase, and the second enzyme is selected from the group consisting of alkaline phosphatase, maltase, $\beta$-galactosidase and cellulase.

7. A method according to claim 1, wherein the steps (a), (b) and (c) of determining the relationships between the concentrations of the first and the second substrates and the response current values further comprises the steps of:

supplying a plurality of solutions including the first or the second substrate respectively at known concentrations to a plurality of the auxiliary testing biosensors;

applying a voltage between the counter electrode and the working electrode of each auxiliary testing biosensor after the set periods of time $T_1$ and $T_2$, $T_1$ and $T_2$ beginning upon supplying each solution to each of the auxiliary testing biosensors; and measuring current values of a set period of time after applying the voltage.

8. A method for measuring concentrations of a first substrate and a second substrate in a sample liquid by using a biosensor having an electrical insulating substrate, an electrode system including a working electrode and a counter electrode, and a reaction layer including a first enzyme that can specifically react with the first substrate, a second enzyme that can specifically react with the second substrate and an electron acceptor;

the method comprising the steps of:
(a) obtaining a response curve a indicating a relationship between a concentration of the first substrate and a response current value measured with an auxiliary testing biosensor for a plurality of solutions having different known concentrations of the first substrate after a set period of time $T_1$, $T_1$ beginning upon supplying a solution including the first substrate to the auxiliary testing biosensor, the set period of time $T_1$ being a time required for at least part of the first substrate to react with the first enzyme;

(b) obtaining a response curve b indicating a relationship between the concentration of the first substrate and a response current value measured with the auxiliary testing biosensor after a set period of time $T_2$, $T_2$ beginning upon supplying the solution including the first substrate to the auxiliary testing biosensor, the set period of time $T_1$ being a time required for at least part of the second substrate to react with the second enzyme;

(c) obtaining a response curve d indicating a relationship between a concentration of the second substrate and a response current value measured with the auxiliary testing biosensor for a plurality of solutions having different known concentrations of the second substrate after the set period of time $T_2$, $T_2$ beginning upon supplying the solution including the second enzyme;

(d) applying a voltage between the working electrode and the counter electrode in the electrode system after the set period of time $T_1$, $T_1$ beginning upon supplying the sample liquid including the first substrate and the second substrate to the biosensor, to measure a response current value $I_1$;

(e) applying a voltage between the working electrode and the counter electrode in the electrode system after the set period of time $T_2$, $T_2$ beginning upon supplying the sample liquid including the first substrate and the second substrate to the biosensor, to measure a response current value $I_2$;

(f) obtaining a concentration of the first substrate in the sample liquid corresponding to the current value $I_1$ based on the response curve a obtained in step (a);

(g) obtaining a response current value $I_1'$ corresponding to the concentration $C_1$ of the first substrate in the sample liquid based on the response curve b obtained in step (b); and (h) obtaining a concentration $C_2$ of the second substrate in the sample liquid corresponding to the current value calculated by subtracting the current value $I_1'$ from the current value $I_2$ based on the response curve d obtained in step (c).

9. A method according to claim 8, wherein the set period of time $T_1$ is 30 seconds or less and the set period of time $T_2$ is 50 seconds or more.

10. A method according to claim 8, wherein the first enzyme is glucose oxidase.

11. A method according to claim 8, wherein the first enzyme is fructose dehydrogenase.

12. A method according to claim 8, wherein the second enzyme is invertase.

13. A method according to claim 8, wherein the second enzyme is selected from the group consisting of hydrolase of sucrose, alkaline phosphatase, maltase, $\beta$-galactosidase and cellulase.

14. A method according to claim 8, wherein the first enzyme is glucose oxidase, and the second enzyme is hydrolase of sucrose.

15. A method according to claim 8, wherein the first enzyme is fructose dehydrogenase, and the second enzyme is hydrolase of sucrose.

16. A method according to claim 8, wherein the first enzyme is selected from the group consisting of glucose oxidase and fructose dehydrogenase, and the second enzyme is selected from the group consisting of hydrolase of sucrose, alkaline phosphatase, maltase, $\beta$-galactosidase and cellulase.

17. A method according to claim 1, wherein the first enzyme is glucose oxidase.

18. A method according to claim 1, wherein the first enzyme is fructose dehydrogenase.

19. A method according to claim 1, wherein the second enzyme is invertase.

20. A method according to claim 1, wherein the second enzyme is selected from the group consisting of hydrolase of sucrose, alkaline phosphatase, maltase, $\beta$-galactosidase and cellulase.

* * * * *